(12) United States Patent
Gruss et al.

(10) Patent No.: US 7,884,247 B2
(45) Date of Patent: Feb. 8, 2011

(54) SALT OF DIMETHYLAMINOMETHYL-PHENYL-CYCLOHEXANE AND CRYSTALLINE FORMS THEREOF

(75) Inventors: Michael Gruss, Aachen (DE); Wolfgang Hell, Aachen (DE); Martin Szelagiewicz, Muenchenstein (CH); Joerg Berghausen, Loerrach (DE); Susan Margaret De Paul, Zurich (CH); Markus Von Raumer, Arlesheim (CH)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/491,238

(22) Filed: Jul. 24, 2006

(65) Prior Publication Data
US 2007/0032552 A1 Feb. 8, 2007

Related U.S. Application Data (60) Provisional application No. 60/702,636, filed on Jul. 27, 2005.

(30) Foreign Application Priority Data
Jul. 22, 2005 (DE) .................. 10 2005 034 974

(51) Int. Cl.
*C07C 209/00* (2006.01)
(52) U.S. Cl. .................. 564/425; 564/304; 514/646
(58) Field of Classification Search .................. 564/425, 564/304; 514/646
See application file for complete search history.

(56) References Cited

U.S. PATENT DOCUMENTS

| 5,733,936 | A | 3/1998 | Buschmann et al. |
| 6,780,891 | B2 * | 8/2004 | Senanayake et al. ........ 514/646 |
| 2004/0242617 | A1 * | 12/2004 | Christoph ................ 514/282 |

FOREIGN PATENT DOCUMENTS

EP 0 753 506 A1 1/1997

OTHER PUBLICATIONS

Berge et al., "Pharmaceutical Salts," J. of Pharmaceutical Sciences, 66 (1): 1-19 (1977).

* cited by examiner

*Primary Examiner*—Sudhakar Katakam
(74) *Attorney, Agent, or Firm*—Crowell & Moring LLP (57) ABSTRACT

Novel 3-[2-(dimethylamino)methyl-(cyclohex-1-yl)]-phenol maleate compounds corresponding to formula I

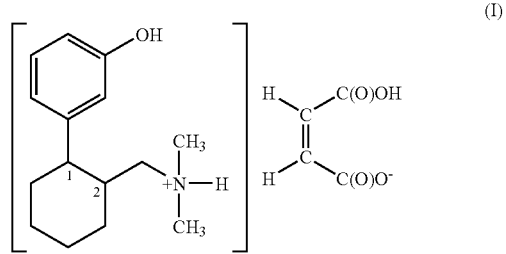

(I)

and processes for preparing these compounds are provided. Pharmaceutical compositions including these compounds and methods of treating or alleviating pain with these compounds are also provided.

18 Claims, 4 Drawing Sheets

SALT OF DIMETHYLAMINOMETHYL-PHENYL-CYCLOHEXANE AND CRYSTALLINE FORMS THEREOF

CROSS-REFERENCE TO RELATED APPLICATIONS

This application claims benefit under 35 U.S.C. §119(e) to U.S. provisional patent application Ser. No. 60/702,636, filed Jul. 27, 2005, and also claims benefit to German patent application Serial No. 10 2005 034 974.9 filed Jul. 22, 2005, the entire disclosures of which are hereby incorporated in their entirety.

FIELD OF THE INVENTION

The present invention relates to salts of maleic acid and 3-[2-(dimethylamino)methyl-(cyclohex-1-yl)]-phenol, preferably in a 1:1 composition, to stable crystalline forms of the salt and to processes for the production thereof, to a pharmaceutical composition and to the use of the salt as a pharmaceutical active ingredient in a composition.

BACKGROUND OF THE INVENTION

EP-A1-0 753 506 describes 3-[2-(dimethylamino)methyl-(cyclohex-1-yl)]-phenols with analgesic action. It is mentioned in the text that salts may also be produced from the free bases, maleic acid not, however, being mentioned as a possible anion. In the Examples, only hydrochlorides are provided, i.e. a salt with a monovalent anion. EP-A1-0 753 506 does not contain any indications as to the stoichiometric ratio in which 3-[2-(dimethylamino)methyl-(cyclohex-1-yl)]-phenols with divalent anions may be present, for example as half- or 1:1 salts. A more detailed investigation of 3-[2-(dimethylamino)methyl-(cyclohex-1-yl)]-phenol hydrochloride has shown that this crystalline solid is distinguished by pronounced polymorphism and forms a plurality of crystalline and also metastable forms. In addition, this hydrochloride has a strong tendency to form hydrates and solvates, which is a considerable disadvantage with regard to the purposeful production of a specific crystalline form. Crystalline 3-[2-(dimethylamino)methyl-(cyclohex-1-yl)]-phenol hydrochloride has additionally proven to be decidedly hygroscopic. This range of properties of 3-[2-(dimethylamino)methyl-(cyclohex-1-yl)]-phenol hydrochloride makes it clear that it is very difficult using this active substance to provide pharmaceutical compositions with reproducible properties which are also retained over a period of storage. To achieve these objectives there would at least be a need for complex protective measures.

SUMMARY OF THE INVENTION

It has now surprisingly been found that 3-[2-(dimethylamino)methyl-(cyclohex-1-yl)]-phenol forms with maleic acid a maleate as a crystalline solid, preferably in a composition exhibiting a ratio of 1:1 of maleic acid anion and 3-[2-(dimethylamino)methyl-(cyclohex-1-yl)]-phenol. It has furthermore surprisingly been found that the maleate is not hygroscopic, is stable in air and does not form any hydrates or solvates. It has also surprisingly been found that 3-[2-(dimethylamino)methyl-(cyclohex-1-yl)]-phenol maleate is able to form only a few, namely two crystalline forms stable at low or at elevated temperature, and that identifiable metastable forms convert into form A, which is stable at room temperature. Form B, which is stable at higher temperatures, may likewise be converted into form A, it being possible for both forms to be present in a mixture at low temperature. Crystalline form A is also distinguished by elevated chemical stability at temperatures of below 100° C. In addition, 3-[2-(dimethylamino)methyl-(cyclohex-1-yl)]-phenol maleate also exhibits valuable biological properties, such as for example good solubility particularly in polar and protic solvents including water, and good bioavailability. Due to its range of properties, 3-[2-(dimethylamino)methyl-(cyclohex-1-yl)]-phenol maleate is outstandingly suitable for the formulation of pharmaceutical compositions.

DETAILED DESCRIPTION

The present invention firstly provides salts of maleic acid with 3-[2-(dimethylamino)methyl-(cyclohex-1-yl)]-phenol, 3-[2-(dimethylamino)methyl-(cyclohex-1-yl)]-phenol maleates of the formula I (I)

being preferred.

The compounds according to the invention, such as compounds of the formula I, each contain a chiral C atom in positions 1 and 2 of the cyclohexane ring. The compounds according to the invention such as the compounds of the formula I comprise all stereoisomers and mixtures of stereoisomers. Diastereomers or mixtures of enantiomeric diastereomers are preferred which exhibit transconfiguration of the phenyl ring and of the dimethylaminomethyl group (1R,2R or 1S,2S configuration), the enantiomer with the absolute configuration (1R,2R) being very particularly preferred.

The structure of the (1R,2R)-enantiomer of 3-[2-(dimethylamino)methyl-(cyclohex-1-yl)]-phenol is shown below:

The compounds of the formula I may be obtained, in a manner similar to the methods described in general in EP-A1-0 753 506 for the production of salts, from the free base and reaction with maleic acid or maleic anhydride in the presence of water. The free base 3-[2-(dimethylamino)methyl-(cyclohex-1-yl)]-phenol may be isolated for example from the hydrochloride described in Examples 9 and 10 of EP-A1-0 753 506. To this end, the hydrochloride is dissolved in an organic solvent, combined with an aqueous inorganic base, for example alkali metal bases or also alkali metal hydrogencarbonates (such as LiOH, NaOH, KOH, $NaHCO_3$ and $KHCO_3$), and the organic phase is isolated. The organic phase may be dried and the base may either be isolated in conventional manner or optionally used directly for salt formation after concentration by evaporation from the solvent.

It has surprisingly been found that salt formation only results in a crystalline form when the temperature is monitored and no temperatures of over 100° C. are applied.

The present invention also provides a process for the production of 3-[2-(dimethylamino)methyl-(cyclohex-1-yl)]-phenol maleate of the formula I, comprising the combination of 3-[2-(dimethylamino)methyl-(cyclohex-1-yl)]-phenol and maleic acid, wherein preferably at least one of the components is present in dissolved or suspended form.

The present invention also provides a process for the production of 3-[2-(dimethylamino)methyl-(cyclohex-1-yl)]-phenol maleate of the formula I, comprising the steps a) dissolving or suspending 3-[2-(dimethylamino)methyl-(cyclohex-1-yl)]-phenol in a solvent, b) mixing the solution or suspension with maleic acid or a solution of maleic acid, and c) isolating the compound of the formula I, the temperature preferably not being above 100° C. in any process step and it also being possible to reverse steps a) and b).

The temperature is preferably no more than 80° C., more preferably no more than 70° C. and particularly preferably no more than 60° C. During dissolution according to process step a), the temperature is generally higher than during mixing according to process step b).

The free base and maleic acid may be used in the molar ratio of 1:1, or maleic acid may also be used in excess, for example in a molar ratio of up to 1.3, preferably up to 1.1. When an excess of the free base is used, no hemimaleates are formed, even if a molar ratio of base to maleic acid of 2:1 is established.

The quantity of 3-[2-(dimethylamino)methyl-(cyclohex-1-yl)]-phenol in the solution may amount for example to 5 to 70 wt. %, preferably 10 to 60 wt. %, more preferably 10 to 50 wt. %, and particularly preferably 15 to 40 wt. %, relative to the solution. The solution of 3-[2-(dimethylamino)methyl-(cyclohex-1-yl)]-phenol may be heated and then optionally cooled to the temperature desired for mixing with maleic acid.

In the process for the production of 3-[2-(dimethylamino) methyl-(cyclohex-1-yl)]-phenol maleate described herein, the maleic acid may in each case also be used in the form of the anhydride thereof.

Inert (compatible) solvents for 3-[2-(dimethylamino)methyl-(cyclohex-1-yl)]-phenol and maleic acid or maleic anhydride are for example aliphatic, cycloaliphatic and aromatic hydrocarbons (hexane, heptane, petroleum ether, cyclohexane, methylcyclohexane, benzene, toluene, xylene), aliphatic halogenated hydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane), ketones (acetone, 2-butanone, methyl isobutyl ketone), carboxylic acid esters and lactones (ethyl or methyl acetate, valerolactone), N-substituted lactams (N-methylpyrrolidone), carboxylic acid amides (dimethylacetamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, 1- or 2-propanol, n-, i- and t-butanol, 1-pentanol, 1-hexanol, 1-heptanol, 1-octanol, ethylene glycol monomethyl ether, ethylene glycol monoethyl ether, diethylene glycol monomethyl- or monoethyl ether) and water. The solvents may be used alone or in a mixture of at least two solvents. Advantageously, physiologically unproblematic solvents are used, which are familiar to the person skilled in the art.

Mixing in process step b) may proceed by means of the slow or rapid addition of one solution to the other solution. One or both solutions may be heated. Mixing may also be performed in such a way, however, that one or both solutions are at room temperature or have been cooled, for example down to −20° C. and more preferably down to −10 to +10° C., most preferably −5 to +5° C. After mixing, the mixture may be heated and cooled again and stirring may continue for a given period. Crystal formation may also be promoted by seeding.

As a rule, a white precipitate forms as early as during mixing, said precipitate being crystalline and readily filterable. Isolation may proceed by decanting, filtration or centrifugation. The crystalline residue may then be dried again, for example by means of heating, vacuum drying or heating under a vacuum, or by means of an optionally heated, inert stream of gas (air, nitrogen, noble gases). The compounds of the formula I are obtained in elevated yields and with elevated purity. As a rule, no or only a few further cleaning steps, such as for example recrystallisation, are necessary and the product may be used directly for the production of pharmaceutical compositions.

The present invention also provides a salt of maleic acid and 3-[2-(dimethylamino)methyl-(cyclohex-1-yl)]-phenol, in particular a salt of the formula I, obtainable by one of the above-described processes.

The compounds of the formula I and the production process according to the invention offer considerable and in part unexpected advantages relative to corresponding hydrochlorides. Since no hydrates and solvates could be characterised, the selection of usable solvents is broad and non-critical. Open handling without particular protective measures is possible due to the stability in air and against moisture. The spontaneous salt formation and formation of crystalline deposits and their good filterability allow processes on an industrial scale The compounds of the formula I are obtained in the salt formation process according to the invention as crystalline solids predominantly in a polymorphic form, which is hereinafter designated form A. Amorphous forms of the compounds of the formula I are simple to obtain for example by means of freeze drying or rapid cooling of solutions. Amorphous compounds of the formula I are not very stable and tend to crystallise in the presence of moisture. They are therefore particularly suitable as a starting material for the purposeful production of crystalline forms.

It has been found that the compounds of the formula I form as crystalline solids polymorphic forms which may be produced purposefully from 3-[2-(dimethylamino)methyl-(cyclohex-1-yl)]-phenol maleate and, due to their stability, are in particular suitable as the active ingredient in the formulation of pharmaceutical compositions. It is known [see for example Z. Jane Li et al. in J. Pharm. Sci., Vol. 88(3), pages 337 to 346 (1999)] that enantiomers result in identical X-ray diffractograms and Raman spectra and thus form the same polymorphic forms. For the purposes of the invention, polymorphic forms of all enantiomers are thus included.

The present invention also provides a crystalline form of 3-[2-(dimethylamino)methyl-(cyclohex-1-yl)]-phenol maleate of the formula I, which exhibits a characteristic X-ray diffraction pattern in the range from 20 to 35° 2θ with pronounced characteristic lines, expressed in d values (Å):

9.4 (vs), 6.8 (m), 5.56 (s), 5.30 (s), 5.22 (s), 4.71 (s), 4.66 (s), 4.24 (m), 4.12 (m), 4.03 (m), 3.98 (s) 3.76 (m), 3.27 (m);

hereinafter designated as form A.

Both above and below, the abbreviations in brackets mean the following: (vs)=very strong intensity, (s)=strong intensity, (m)=moderate intensity, (w)=weak intensity, and (vw)=very weak intensity.

The present invention also provides a crystalline form A of 3-[2-(dimethylamino)methyl-(cyclohex-1-yl)]-phenol maleate of the formula I, which exhibits a characteristic X-ray diffraction pattern with following pronounced reflections.

| 2theta | rel. intensity |
| --- | --- |
| 9.38 | 100 |
| 9.94 | 5 |
| 10.35 | 8 |
| 12.76 | 6 |
| 13.07 | 20 |
| 13.49 | 7 |
| 15.94 | 43 |
| 16.72 | 52 |
| 16.98 | 40 |
| 17.54 | 15 |
| 18.86 | 61 |
| 19.04 | 48 |
| 19.28 | 8 |
| 20.01 | 5 |
| 20.57 | 6 |
| 20.96 | 24 |
| 21.57 | 23 |
| 22.03 | 20 |
| 22.33 | 30 |
| 23.69 | 15 |
| 24.84 | 8 |
| 25.01 | 9 |
| 25.71 | 11 |
| 26.35 | 7 |
| 26.75 | 13 |
| 27.24 | 16 |
| 27.66 | 9 |
| 27.95 | 6 |
| 28.40 | 5 |
| 28.68 | 9 |
| 29.87 | 6 |
| 30.76 | 8 |
| 31.37 | 4 |
| 31.67 | 4 |
| 31.99 | 6 |
| 32.53 | 4 |
| 32.80 | 5 |
| 33.55 | 7 |
| 35.20 | 5 |
| 36.93 | 5 |
| 37.58 | 5 |
| 44.54 | 6 |
| 45.70 | 4 |

The above Table states the peak positions (in 2 theta) and the relative intensities of the peaks, the highest intensity peak here being normalised to a relative intensity of 100.

The present application furthermore provides a crystalline form A of 3-[2-(dimethylamino)methyl-(cyclohex-1-yl)]-phenol maleate of the formula I (polymorph A), characterised by a powder diffractogram comprising one or more the following reflections: 9.38 (100), 9.94 (5) and 10.35 (8) (in each case ±0.5 in 2 theta, relative intensity in brackets). The powder diagram may preferably additionally comprise one or more of the following reflections: 12.76 (6), 15.94 (43), 17.54 (15), 19.28 (8), 28.68 (9) and 31.99 (6) (in each case ±0.2 in 2 theta, relative intensity in brackets).

The present invention also provides a crystalline form A of 3-[2-(dimethylamino)methyl-(cyclohex-1-yl)]-phenol maleate of the formula I, which exhibits a characteristics Raman spectrum with characteristic lines, expressed in wavenumbers (cm-1):

| Position (cm-1) | Intensity |
| --- | --- |
| 3060 | m |
| 3040 | m |
| 3021 | m |
| 2986 | m |
| 2966 | s |
| 2933 | s |
| 2920 | s |
| 2895 | m |
| 2879 | m |
| 2856 | s |
| 2812 | w |
| 1690 | m |
| 1616 | m |
| 1601 | m |
| 1569 | vw |
| 1467 | m |
| 1443 | m |
| 1412 | w |
| 1389 | m |
| 1361 | w |
| 1351 | m |
| 1332 | w |
| 1322 | w |
| 1306 | w |
| 1295 | w |
| 1289 | w |
| 1273 | m |
| 1247 | m |
| 1227 | w |
| 1211 | m |
| 1177 | w |
| 1167 | w |
| 1122 | vw |
| 1106 | w |
| 1081 | w |
| 1076 | w |
| 1055 | m |
| 1047 | m |
| 1025 | w |
| 999 | vs |
| 971 | vw |
| 957 | m |
| 929 | w |
| 901 | w |
| 855 | m |
| 843 | m |
| 817 | w |
| 796 | w |
| 754 | m |
| 707 | vw |
| 676 | vw |
| 635 | m |
| 614 | w |
| 572 | vw |

-continued

| Position (cm-1) | Intensity |
|---|---|
| 536 | m |
| 514 | vw |
| 486 | vw |
| 468 | vw |
| 454 | w |
| 425 | vw |
| 400 | w |
| 359 | w |
| 345 | w |
| 328 | m |
| 292 | m |
| 272 | m |
| 247 | s |
| 188 | w |
| 118 | vs |
| 105 | vs |
| 81 | vs |

The invention further provides a crystalline form A of 3-[2-(dimethylamino)methyl-(cyclohex-1-yl)]-phenol maleate of the formula I comprising one or more of the following characteristic bands in the Raman spectrum, in each case expressed in wavenumbers (cm-1): 118 (vs), 188 (w), 400 (w), 676 (w), 2812 (w), 2879 (m), preferably one or more of the following bands:
118 (vs), 188 (w), 292 (m), 328 (m), 359 (w), 400 (w), 486 (vw), 676 (w), 901 (w), 1025 (w), 1273 (m), 1351 (m), 1412 (w), 1569 (vw), 1601 (m), 1690 (m), 2812 (w), 2879 (m), 2986 (m), 3060 (m).

Figure 1:
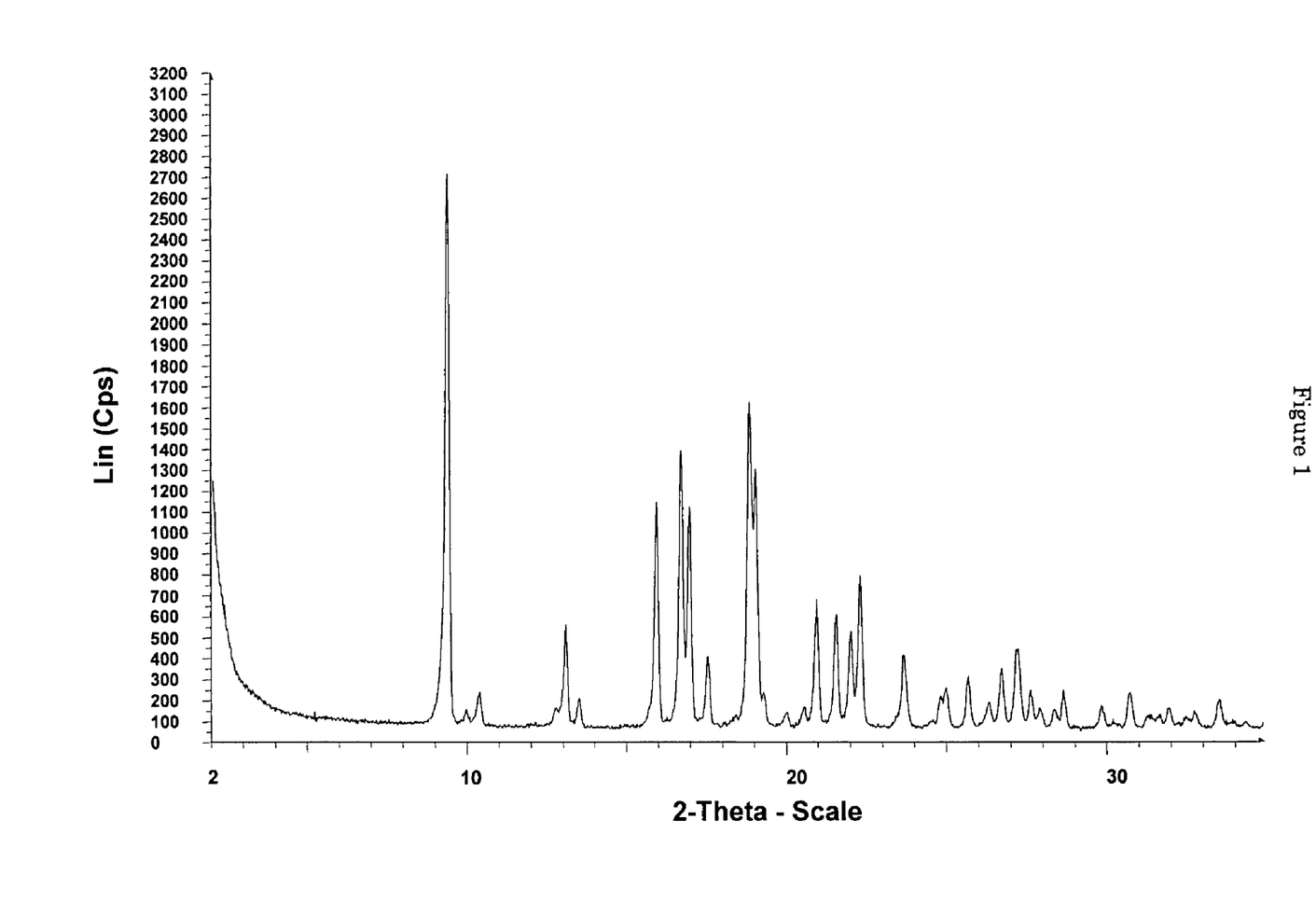
FIG. 1 shows the X-ray diffraction pattern of polymorphic form A

The present invention also provides a crystalline form A of 3-[2-(dimethylamino)methyl-(cyclohex-1-yl)]-phenol maleate of the formula I, which exhibits an X-ray diffraction pattern as illustrated in FIG. 1.

Figure 2:
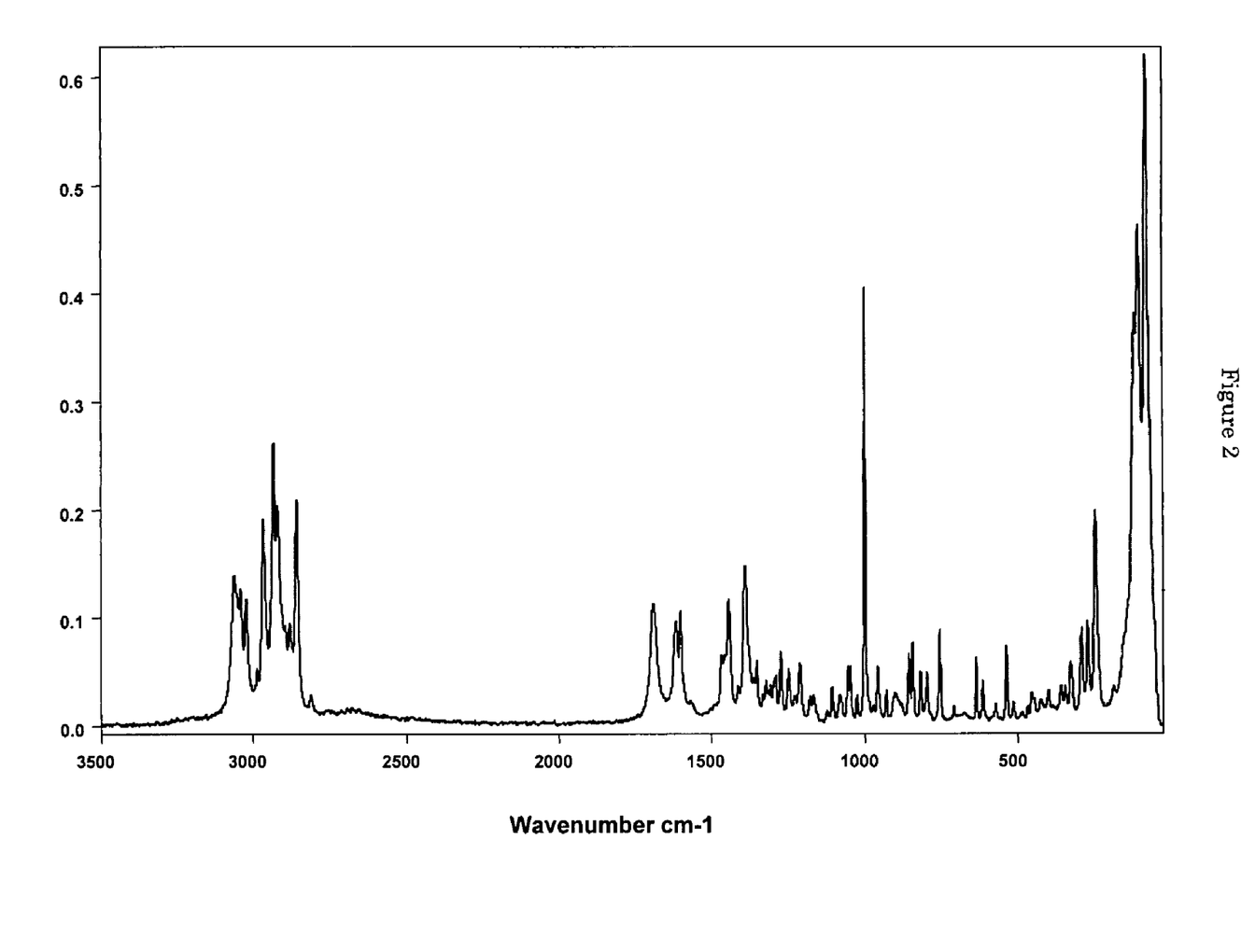
FIG. 2 shows the Raman spectrum of polymorphic form A

The present invention also provides a crystalline form A of 3-[2-(dimethylamino)methyl-(cyclohex-1-yl)]-phenol maleate of the formula I, which exhibits a Raman spectrum as illustrated in FIG. 2.

The crystalline form A is the thermodynamically most stable form at low temperature up to for example approx. 100° C. and additionally exhibits excellent chemical and physical stability. Polymorph A is stable and insensitive even to the influence of atmospheric humidity at elevated relative atmospheric humidities of up to 90%, even over a relatively long period. No water absorption, no formation of hydrates and no conversion into other crystalline forms is observed under normal conditions. Polymorph A also exhibits no phase transformations in air and the presence of moisture. Polymorph A also does not change under elevated pressure or on grinding, and conversion into other crystalline forms on exposure to relatively high pressure does not occur. Polymorph A is also non-hygroscopic and absorbs only small quantities of surface water. Under these conditions, polymorph A also does not form any solvates and no conversion is observed in contact with solvents. Solubility in polar solvents is very good. The melting point is approx. 167° C. and the enthalpy of fusion is approx. 135 J/g. Polymorph A may be produced as a solid powder with desired average particle sizes which lie as a rule in the range from 1 μm to approx. 500 μm. Because of these properties, the crystalline form A is extremely well suited to the production of pharmaceutical formulations.

The compound of the formula I forms a further crystalline form B which is thermodynamically stable at elevated temperatures, and which is likewise stable under normal conditions in air and with the exclusion of atmospheric humidity. The crystalline form B may also be handled in such a way that it may be used for the production of pharmaceutical compositions.

The present invention also provides a crystalline form of 3-[2-(dimethylamino)methyl-(cyclohex-1-yl)]-phenol maleate of the formula I, which exhibits a characteristic X-ray diffraction pattern in the range from 2° to 35° 2θ with pronounced characteristic lines, expressed in d values (Å):
10.6 (m), 7.5 (m), 7.3 (m), 6.1 (s), 5.29 (s) 4.88 (m), 4.72 (m), 4.47 (vs), 4.43 (m), 4.26 (m), 4.24 (m), 3.99 (s), 3.71 (m), 3.52 8m), 3.30 (s);

hereinafter designated as form B.

The present invention also provides a crystalline form B of 3-[2-(dimethylamino)methyl-(cyclohex-1-yl)]-phenol maleate of the formula I, which exhibits a characteristic X-ray diffraction pattern with following pronounced reflections.

| Theta | rel. intensity |
|---|---|
| 8.36 | 18 |
| 11.85 | 20 |
| 12.19 | 20 |
| 13.41 | 12 |
| 14.50 | 49 |
| 14.83 | 11 |
| 16.77 | 58 |
| 18.16 | 17 |
| 18.78 | 28 |
| 19.84 | 100 |
| 20.00 | 17 |
| 20.84 | 19 |
| 20.97 | 16 |
| 21.19 | 12 |
| 22.27 | 33 |
| 22.64 | 7 |
| 22.85 | 11 |
| 23.95 | 18 |
| 24.53 | 7 |
| 24.85 | 8 |
| 25.26 | 16 |
| 25.97 | 8 |
| 26.66 | 12 |
| 27.00 | 29 |
| 27.18 | 13 |
| 27.48 | 8 |
| 28.21 | 4 |
| 29.10 | 6 |
| 29.41 | 9 |
| 29.90 | 8 |
| 30.49 | 10 |
| 31.32 | 6 |
| 33.14 | 6 |
| 33.88 | 5 |
| 34.32 | 4 |
| 34.99 | 10 |
| 36.32 | 3 |
| 36.88 | 4 |
| 37.86 | 4 |
| 38.35 | 10 |
| 42.11 | 5 |
| 42.78 | 3 |
| 43.05 | 3 |
| 43.62 | 6 |
| 44.35 | 4 |
| 46.83 | 6 |
| 47.80 | 3 |
| 48.35 | 3 |

The above Table states the peak positions (in 2 theta) and the relative intensities of the peaks, the highest intensity peak here being normalised to a relative intensity of 100.

The present invention furthermore provides polymorph B of 3-[2-(dimethylamino)methyl-(cyclohex-1-yl)]-phenol maleate of the formula I, characterised by a powder diffractogram comprising one or more the following reflections: 8.36 (18), 14.5 (49) and 14.83 (11) (in each case ±0.5 in 2 theta, relative intensity in brackets). The powder diagram may preferably additionally comprise one or more of the following reflections: 11.85 (20), 12.19 (20), 18.16 (17), 22.85 (11), 29.1 (6) and 29.41 (6) (in each case ±0.2 in 2 ts).

The present invention also provides a crystalline form B of 3-[2-(dimethylamino)methyl-(cyclohex-1-yl)]-phenol maleate of the formula I, which exhibits a characteristic Raman spectrum with characteristic lines, expressed in wavenumbers (cm-1):

| Position (cm-1) | Intensity |
|---|---|
| 3045 | vs |
| 3028 | m |
| 2974 | s |
| 2953 | s |
| 2928 | vs |
| 2896 | s |
| 2856 | s |
| 2829 | m |
| 1703 | s |
| 1621 | m |
| 1612 | m |
| 1583 | m |
| 1480 | vw |
| 1459 | m |
| 1446 | m |
| 1401 | vw |
| 1385 | m |
| 1360 | s |
| 1227 | vw |
| 1324 | w |
| 1313 | m |
| 1309 | m |
| 1295 | m |
| 1282 | m |
| 1253 | w |
| 1220 | w |
| 1211 | m |
| 1197 | m |
| 1178 | w |
| 1162 | m |
| 1124 | w |
| 1104 | w |
| 1081 | w |
| 1076 | w |
| 1052 | m |
| 1010 | w |
| 999 | vs |
| 971 | vw |
| 956 | w |
| 933 | w |
| 890 | w |
| 875 | m |
| 858 | m |
| 841 | s |
| 816 | m |
| 794 | m |
| 750 | m |
| 708 | vw |
| 628 | w |
| 620 | w |
| 605 | vw |
| 578 | w |
| 573 | w |
| 538 | m |
| 507 | vw |
| 472 | w |
| 455 | w |
| 449 | w |
| 418 | w |
| 372 | w |
| 340 | m |
| 307 | w |

-continued

| Position (cm-1) | Intensity |
|---|---|
| 272 | m |
| 246 | s |
| 229 | m |
| 101 | vs |
| 83 | vs |

The present invention further provides a crystalline form B of 3-[2-(dimethylamino)methyl-(cyclohex-1-yl)]-phenol maleate of the formula I comprising one or more of the following characteristic bands in the Raman spectrum, in each case expressed in wavenumbers (cm-1): 229 (vs), 875 (w) and 2829 (m), preferably one or more of the following bands:
229 (m), 307 (w), 372 (w), 605 (vw), 875 (m), 890 (w), 1010 (w), 1197 (m), 1401 (vw), 1480 (vw), 1583 (m), 1703 (s), 2829 (m), 2953 (s).

Figure 3:
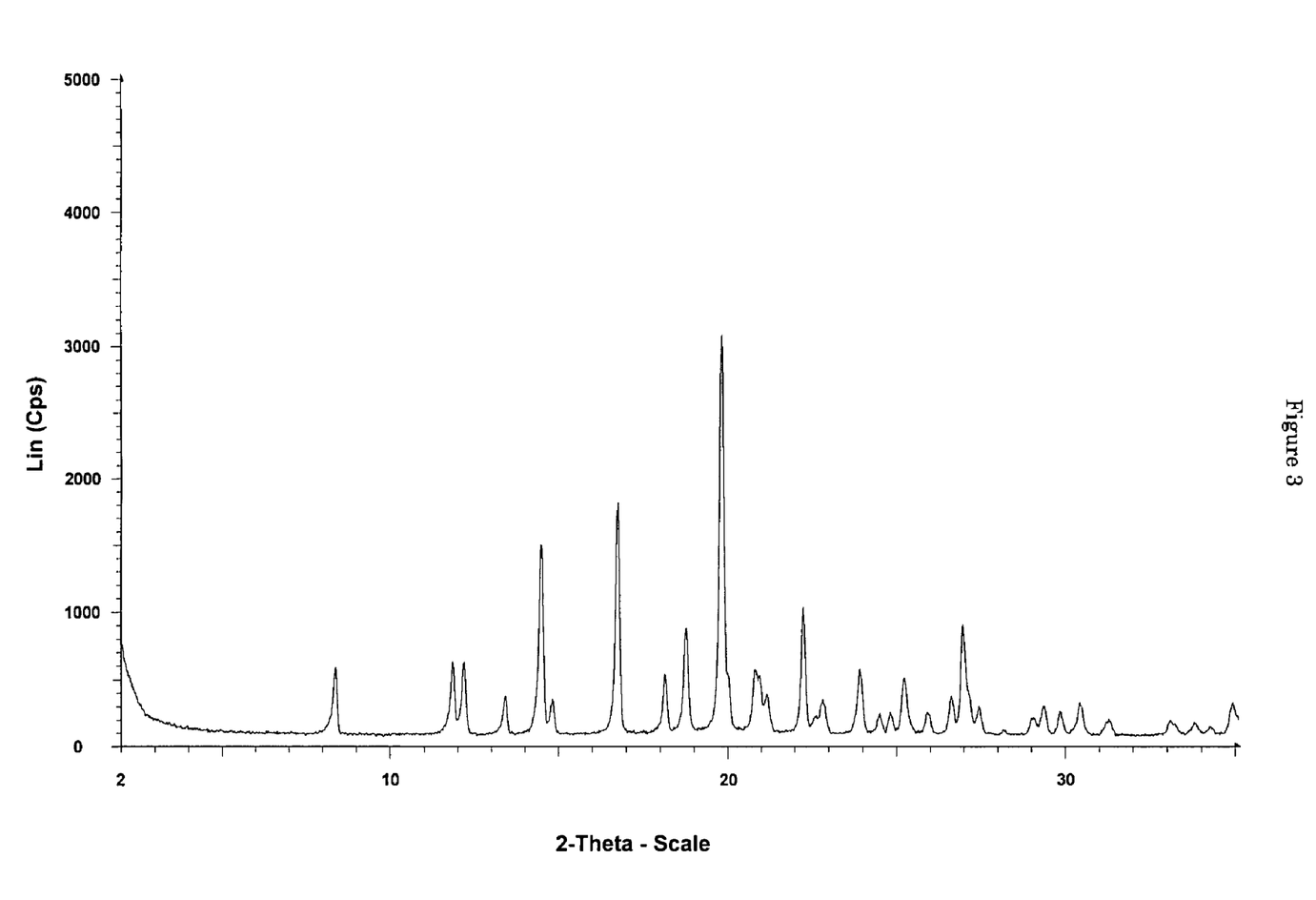
FIG. 3 shows the X-ray diffraction pattern of polymorphic form B

The invention also provides a crystalline form B of 3-[2-(dimethylamino)methyl-(cyclohex-1-yl)]-phenol maleate of the formula I, which exhibits an X-ray diffraction pattern as illustrated in FIG. 3.

Figure 4:
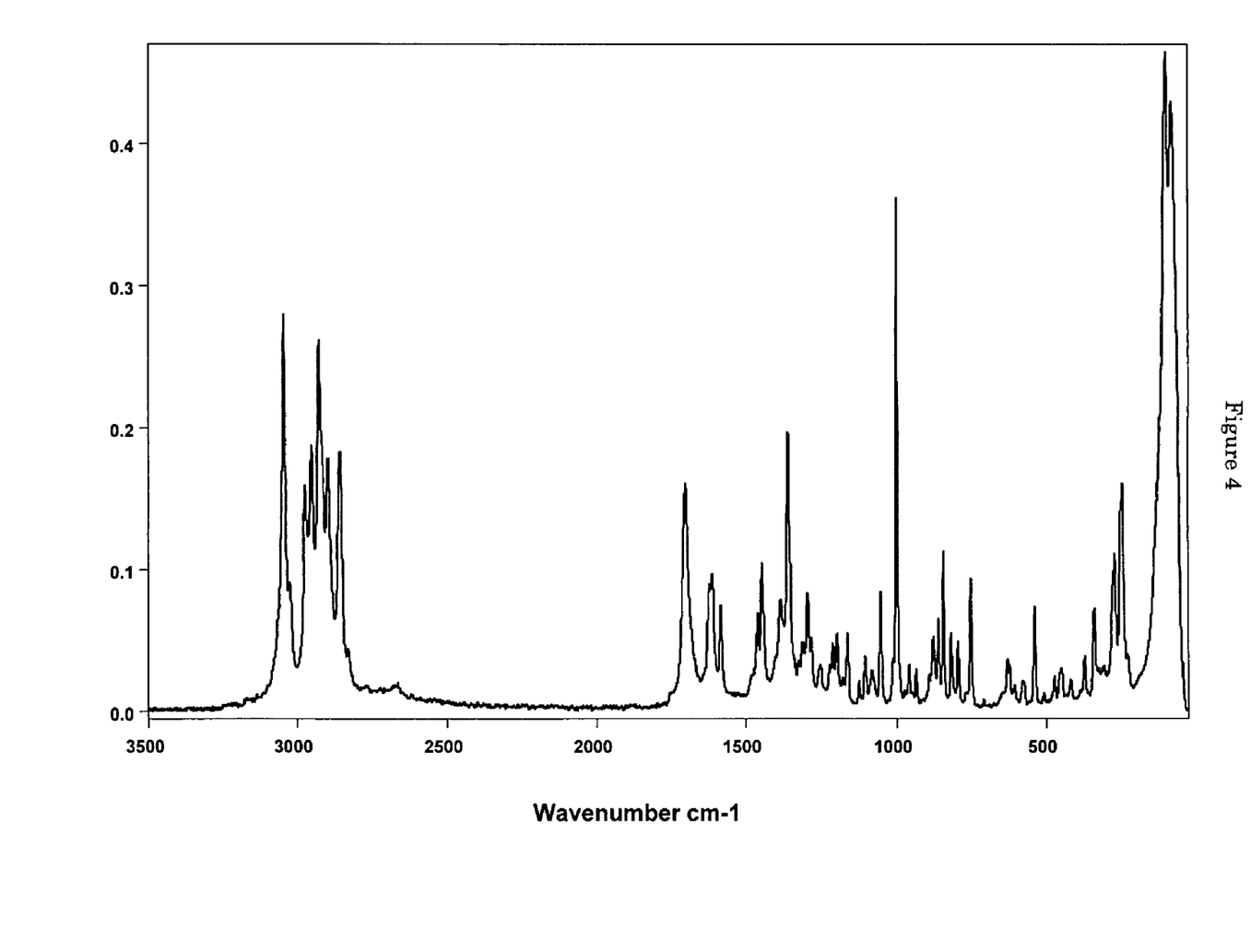
FIG. 4 shows the Raman spectrum of polymorphic form B

The invention further provides a crystalline form B of 3-[2-(dimethylamino)methyl-(cyclohex-1-yl)]-phenol maleate of the formula I, which exhibits a Raman spectrum as illustrated in FIG. 4.

The polymorphic form B may convert into the crystalline form A. Forms A and B form an enantiotropic system with a transition point or range of approx. 100 to 120° C. The present invention therefore also provides mixtures of crystalline forms A and B in any per se desired quantity ratios.

Crystalline form B is the thermodynamically most stable form at elevated temperatures, for example approx. at least 100° C. or more. Polymorph B additionally exhibits excellent chemical stability at elevated temperatures, even in the presence of atmospheric humidity. Its physical stability is lower, since at elevated pressure, and also at elevated temperatures with or without the influence of moisture, conversion into polymorph A occurs. However, no water absorption and no hydrate formation is observed. Polymorph B also does not form any solvates. In contact with solvents, conversion into crystalline form A may take place. Solubility in polar solvents is very good and comparable with the solubility of polymorph A. The melting point is approx. 178° C. and the enthalpy of fusion is approx. 125 J/g. Polymorph B may be produced as solid powder with desired average particle sizes which lie as a rule in the range from 1 μm to approx. 500 μm. It is advisable to store the crystalline form B under dry protective gas (nitrogen).

The polymorphic forms may be produced using per se known crystallisation processes from the salt 3-[2-(dimethylamino)methyl-(cyclohex-1-yl)]-phenol maleate, for example stirring of suspensions (establishment of phase equilibria), precipitation, recrystallisation, or evaporation of solvents. Dilute, saturated or supersaturated solutions may be used, with or without seeding with a crystal nucleating agent. The temperatures for forming solutions may amount to up to 100° C. Crystallisation may be initiated by cooling to approx. −100° C. to 30° C., and preferably −30° C. to 20° C., it being possible for cooling to proceed continuously or stepwise. To produce solutions or suspensions, amorphous or crystalline starting materials may be used, in order to achieve high concentrations in solutions and to obtain other crystalline forms.

The present invention also provides a process for the production of the crystalline form A from 3-[2-(dimethylamino)methyl-(cyclohex-1-yl)]-phenol maleate, wherein
a) a pulverulent, solid, amorphous form of 3-[2-(dimethylamino)methyl-(cyclohex-1-yl)]-phenol maleate is treated with a water vapour-containing inert gas; or
b) a suspension of the amorphous form of 3-[2-(dimethylamino)methyl-(cyclohex-1-yl)]-phenol maleate is produced in a solvent as carrier and stirred until the crystalline form A is fully formed; or
c) 3-[2-(dimethylamino)methyl-(cyclohex-1-yl)]-phenol maleate is dissolved in a solvent and then precipitated; or
d) 3-[2-(dimethylamino)methyl-(cyclohex-1-yl)]-phenol and maleic acid are combined, wherein preferably at least one of these components is in dissolved or suspended form, and the resultant product is isolated, providing that the temperature does not exceed 100° C.

The temperature in process steps a) and b) preferably amounts to at most 40° C. and the process is particularly preferably performed at room temperature. Inert gases are for example air, nitrogen and noble gases, air being particularly preferred for reasons of economic viability. The relatively humidity of the gases may amount for example to 40 to 90% and preferably 60 to 90%. The treatment time in process step a) depends substantially on particle size and relative humidity and may amount for example to 5 to 100 hours. In process step a), polymorph B may also be formed in addition to form A, if the relative atmospheric humidity is too low and/or the treatment time is too short. After isolation, the crystalline residue may be dried in conventional manner, temperatures of over 100° C. conveniently being avoided.

Process step b) is preferably performed at approx. −20° to 40° C. and particularly preferably at −5° C. to 25° C. (approx. room temperature). Solvents which may be considered have been stated above. The treatment time in process step b) may amount to 5 to 100 hours. After isolation, the solvent or solvent mixture used may be removed in conventional manner by means of known drying processes.

In process step c), the crystalline form A, B or the amorphous form of 3-[2-(dimethylamino)methyl-(cyclohex-1-yl)]-phenol maleate may be used for the production of solutions. The concentration of 3-[2-(dimethylamino)methyl-(cyclohex-1-yl)]-phenol maleate in the solution depends on the selected temperature and on the solvent. The dissolved quantity may amount to for example from 0.5 to 50, preferably 0.5 to 30, more preferably 0.5 to 20 and particularly preferably 1 to 15 weight percent, relative to the solvent. The dissolution temperature may amount to up to 100° C. and preferably up to 60° C. The solution may also be produced at room temperature, if a solvent having elevated solvency is used, for example water, acetone, dimethylformamide, dimethyl sulfoxide, methanol, ethanol, N-methylpyrrolidone and propylene glycol. Precipitation may proceed by means of cooling, partial or complete removal of the solvent, addition of a precipitating agent (non-solvent, for example heptane or methyl t-butyl ether) or a combination of these measures. Cooling may mean slow cooling or also quenching to temperatures of down to −20° C. and preferably down to 0° C. The solvent may proceed by heating, in a gas stream, application of a vacuum or a combination of these measures. Heating to remove solvent means a temperature of at most 70° C. and preferably at most 50° C. in process step c). Precipitation processes according to process step c) are preferably used to produce the polymorphic form A.

In process step d), the temperature is preferably no more than 80° C., more preferably no more than 70° C. and particularly preferably no more than 60° C. During dissolution or suspension of a component, the temperature is generally higher than during mixing.

The present invention also provides a salt of the formula I of maleic acid and 3-[2-(dimethylamino)methyl-(cyclohex-1-yl)]-phenol in crystalline form A (polymorph A) obtainable by a process according to one of the above-described processes.

While production of the polymorphic form A is relatively non-critical, the polymorphic form B may only be obtained using a special process. It has surprisingly been found that form B is obtainable reproducibly using an evaporation process, a specific combination of solvent and elevated evaporation temperatures.

The present invention accordingly also provides a process for the production of crystalline form B of 3-[2-(dimethylamino)methyl-(cyclohex-1-yl)]-phenol maleate, wherein 3-[2-(dimethylamino)methyl-(cyclohex-1-yl)]-phenol maleate is dissolved in a mixture of tetrahydrofuran and water in the volume ratio of 0.8:1.2 to 1.2:0.8, and then the solvent mixture is removed completely at a temperature of at least 80° C. Lower evaporation temperatures in an open atmosphere are also possible, for example at room temperature in an open vessel (contact with atmospheric humidity).

Tetrahydrofuran (THF) and water preferably exhibit a volume ratio of 1:1. Prior to removal of the solvent mixture, the solution may be stirred for a given period, for example up to 24 hours at elevated temperature (approx. 80 to 100° C.). To remove the solvent mixture, a gas stream may additionally be used and/or a vacuum applied. Heating to remove solvent means a temperature of at least 80° C. and preferably up to approx. 120° C. and particularly preferably 90 to 100° C. The solvent is particularly preferably removed by distillation in a rotary evaporator. The quantity of 3-[2-(dimethylamino)methyl-(cyclohex-1-yl)]-phenol maleate in the mixture of THF and water may amount to 0.5 to 20, preferably 0.5 to 10 weight percent, relative to the THF and water mixture.

It has also been found that the establishment of phase equilibria by means of stirring suspensions at temperatures of at least 120° C. leads to the formation of crystalline form B.

The present invention also provides a salt of the formula I of maleic acid and 3-[2-(dimethylamino)methyl-(cyclohex-1-yl)]-phenol in crystalline form B (polymorph B) obtainable by a process according to one of the above-described processes.

Due to its favourable overall range of properties, 3-[2-(dimethylamino)methyl-(cyclohex-1-yl)]-phenol maleate is excellent as an active ingredient for pharmaceutical compositions and very particularly for analgesic medicines. Accordingly, the invention also provides the use of 3-[2-(dimethylamino)methyl-(cyclohex-1-yl)]-phenol maleate of the formula I as an active ingredient in pharmaceutical preparations, preferably as an active ingredient in analgesics. Here too, as throughout the application, preferred diastereomers or mixtures of enantiomeric diastereomers are those which exhibit transconfiguration of the phenyl ring and of the dimethylaminomethyl group (1R,2R or 1S,2S configuration), the enantiomer with the absolute configuration (1R,2R) being very particularly preferred.

The present invention also provides a pharmaceutical composition containing an active quantity of 3-[2-(dimethylamino)methyl-(cyclohex-1-yl)]-phenol maleate of the formula I and a pharmaceutical excipient or a pharmaceutical diluent.

In the composition, the compound of the formula I may be present as crystalline form A, crystalline form B or a mixture of forms A and B. The crystalline form A is preferably present.

The quantity of compounds of the formula I depends substantially on the type of the formulation and on the desired dosage during the period of administration. The quantity of the particular salts according to the invention to be administered to the patient may vary and is for example dependent on the weight or age of the patient and on the mode of administration, the indication and the severity of the complaint. Conventionally, at least one such compound is administered in a quantity of 0.005 to 5000 mg/kg, preferably of 0.05 to 500 mg/kg, of patient body weight.

Oral formulations may comprise solid formulations, for example tablets, capsules, pills and pastilles. Oral formulations may also comprise liquid formulations, for example solutions, suspensions, syrups or elixirs. Liquid and solid formulations also cover incorporation of the compounds of the formula I in solid or liquid foodstuffs. Liquids additionally cover solutions for parenteral administration, such as for example infusion or injection.

The compounds of the formula I and the crystalline forms may be used directly as powder (micronised particles), granules, suspensions or solutions, or they may be mixed with other pharmaceutically acceptable ingredients and components and then pulverised, in order then to introduce the powder into hard or soft gelatine capsules, to press it into tablets, pills or pastilles, or in order to suspend or dissolve the powder in an excipient for the production of suspensions, syrups or elixirs. Tablets, pills or pastilles may be provided with a coating after pressing.

Pharmaceutically acceptable ingredients and components for the various types of the formulation are known per se. They may for example comprise binders such as synthetic or natural polymers, pharmaceutical excipients, lubricants, surfactants, sweeteners and aroma substances, coating agents, preservatives, colorants, thickeners, auxiliary substances, antimicrobial agents and excipients for the various types of the formulation.

Examples of binders are gum arabic, gum tragacanth, acacia gum and biodegradable polymers such as homo- or copolyesters of dicarboxylic acids, alkylene diols, polyalkylene glycols and/or aliphatic hydroxycarboxylic acids; homo- or copolyamides of dicarboxylic acids, alkylene diamines, and/or aliphatic aminocarboxylic acids; corresponding polyester-polyamide copolymers, polyanhydrides, polyorthoesters, polyphosphazenes and polycarbonates. Biodegradable polymers may be linear, branched or crosslinked. Specific examples are polyglycolic acid, polylactic acid, and poly-d,l-lactic/glycolic acid. Other examples of polymers are water-soluble polymers such as for example polyoxaalkylenes (polyoxaethylene, polyoxapropylene and copolymers thereof, polyacrylamides and hydroxyalkylated polyacrylamides, polymaleic acid and esters or amides thereof, polyacrylic acid and esters or amides thereof, polyvinyl alcohol and esters or ethers thereof, polyvinylimidazole, polyvinylpyrrolidone, and natural polymers such as for example chitosan.

Examples of pharmaceutical excipients are phosphates such as dicalcium phosphate.

Examples of lubricants are natural or synthetic oils, fats, waxes or fatty acid salts such as magnesium stearate.

Surfactants (surface-active agents) may be anionic, cationic, amphoteric or neutral. Examples of surfactants are lecithin, phospholipids, octyl sulfate, decyl sulfate, dodecyl sulfate, tetradecyl sulfate, hexadecyl sulfate and octadecyl sulfate, sodium oleate or sodium caprate, 1-acylaminoethane 2-sulfonic acids such as 1-octanoylaminoethane 2-sulfonic acid, 1-decanoylaminoethane 2-sulfonic acid, 1-dodecanoylaminoethane 2-sulfonic acid, 1-tetradecanoylaminoethane 2-sulfonic acid, 1-hexadecanoylaminoethan-2-sulfonic acid, and 1-octadecanoylaminoethane 2-sulfonic acid, bile acids, salts and derivatives thereof, such as for example cholic acid, deoxycholic acid, taurocholic acid, taurodeoxycholic acid and sodium glycocholates, sodium caprate, sodium laurate, sodium oleate, sodium lauryl sulfate, sodium cetyl sulfate, sulfated castor oil, sodium dioctyl sulfosuccinate, cocamidopropyl betaine and lauryl betaine, fatty alcohols, cholesterol, glycerol mono- or distearate, glycerol mono- or dioleate, glycerol mono- or dipalmitate, and polyoxyethylene stearate.

Examples of sweeteners are sucrose, fructose, lactose or aspartame.

Examples of aroma substances are peppermint, oil of wintergreen or fruit essences such as cherry or orange essence.

Examples of coating agents are gelatine, waxes, shellac, sugar or biodegradable polymers.

Examples of preservatives are methyl- or propylparaben, sorbic acid, chlorobutanol and phenol.

Examples of auxiliary substances are fragrance substances.

Examples of thickeners are synthetic polymers, fatty acids, fatty acid salts, fatty acid esters and fatty alcohols.

Examples of liquid excipients are water, alcohols (ethanol, glycerol, propylene glycol, liquid polyethylene glycols), polytriazines and oils. Examples of solid excipients are talcum, aluminas, microcrystalline cellulose, silicon dioxide, aluminium oxide and similar solids.

The composition according to the invention may also contain isotonic agents such as for example sugar, physiological buffers and sodium chloride.

The composition according to the invention may also be formulated as an effervescent tablet or effervescent powder, which disintegrates in an aqueous environment when drinkable solutions or suspensions are prepared.

A syrup or elixir may contain the compound of the formula I, a sugar such as sucrose or fructose as sweetener, a preservative (methylparaben), a colorant and a flavouring agent (aroma substances).

The composition according to the invention may also comprise formulations which exhibit delayed and controlled active ingredient release on contact with bodily fluids of the gastrointestinal tract, in order to achieve a substantially constant and effective level of the active ingredient in the blood plasma. The compounds of the formula I may to this end be embedded in a polymer matrix of a biodegradable polymer, a water-soluble polymer or both polymers, optionally together with a suitable surfactant. In this context, embedding may mean the incorporation of microparticles into the polymer matrix. Formulations exhibiting delayed and controlled active ingredient release may be obtained by encapsulation of dispersed microparticles or emulsified microdroplets using known dispersion and emulsion coating technologies.

The compounds of the formula I may also be used together with at least one further pharmaceutical active ingredient for combination therapies. To this end, at least one further active ingredient may additionally be dispersed or dissolved in the composition according to the invention.

The invention also provides the use of 3-[2-(dimethylamino)methyl-(cyclohex-1-yl)]-phenol maleate of the formula I to produce a pharmaceutical composition, in particular for the treatment of pain.

The invention further provides a method for the treatment of pain, in which an active quantity of 3-[2-(dimethylamino)methyl-(cyclohex-1-yl)]-phenol maleate of the formula I is administered to a patient suffering from pain.

The pharmaceutical preparation according to the invention (the pharmaceutical composition according to the invention) is preferably suitable for the treatment and/or prevention of pain, preferably selected from the group consisting of acute pain, chronic pain, neuropathic pain and visceral pain; of migraine; depression; neurodegenerative diseases, preferably selected from the group consisting of Parkinson's disease, Alzheimer's disease, Huntington's chorea and multiple sclerosis; cognitive disorders, preferably cognitive deficiency states, particularly preferably attention deficit syndrome (ADS), panic attacks; epilepsy; coughing; urinary incontinence; diarrhoea; pruritus; schizophrenia; cerebral ischaemia; muscle spasms; cramps; disorders of food intake, preferably selected from the group consisting of bulimia, cachexia, anorexia and obesity; alcohol and/or drug abuse (in particular nicotine and/or cocaine abuse) and/or abuse of medicines; alcohol and/or drug dependency (in particular nicotine and/or cocaine dependency) and/or dependency on medicines, preferably for prevention and/or reduction of withdrawal symptoms associated with alcohol and/or drug dependency (in particular nicotine and/or cocaine dependency) and/or dependency on medicines; development of tolerance phenomena with regard to medicines; in particular with regard to opioids; gastro-oesophageal reflux syndrome; for diuresis; for antinatriuresis; for influencing the cardiovascular system; for anxiolysis; for increasing vigilance; for increasing libido, for modulating locomotor activity, and for local anaesthesia.

The pharmaceutical preparation according to the invention (the pharmaceutical composition according to the invention) is particularly preferably suitable for the treatment and/or prevention of pain, preferably of acute pain, chronic pain, neuropathic pain or visceral pain; depression; epilepsy; Parkinson's disease; alcohol and/or drug abuse (in particular nicotine and/or cocaine abuse) and/or abuse of medicines; alcohol and/or drug dependency (in particular nicotine and/or cocaine dependency) and/or dependency on medicines; preferably for prevention and/or reduction of withdrawal symptoms associated with alcohol and/or drug dependency (in particular nicotine and/or cocaine dependency) and/or dependency on medicines; development of tolerance phenomena with regard to medicines, in particular with regard to opioids; or for anxiolysis.

The pharmaceutical preparation according to the invention is very particularly preferably suitable for the prevention and/or treatment of pain, preferably acute pain, chronic pain, neuropathic pain or visceral pain.

It is particularly preferred to use at least one salt according to the invention, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, and optionally one or more pharmaceutically compatible auxiliary substances for the production of a pharmaceutical preparation for the prevention and/or treatment of pain, preferably selected from the group consisting of acute pain, chronic pain, neuropathic pain and visceral pain, of migraine, depression, neurodegenerative diseases, preferably selected from the group consisting of Parkinson's disease, Alzheimer's disease, Huntington's chorea and multiple sclerosis, cognitive disorders, preferably cognitive deficiency states, particularly preferably attention deficit syndrome (ADS), panic attacks, epilepsy, coughing, urinary incontinence, diarrhoea, pruritus, schizophrenia, cerebral ischaemia, muscle spasms, cramps, disorders of food intake, preferably selected from the group consisting of bulimia, cachexia, anorexia and obesity, alcohol and/or drug abuse (in particular nicotine and/or cocaine abuse) and/or abuse of medicines; alcohol and/or drug dependency (in particular nicotine and/or cocaine dependency) and/or dependency on medicines; preferably for prevention and/or reduction of withdrawal symptoms associated with alcohol and/or drug dependency (in particular nicotine and/or cocaine dependency) and/or dependency on medicines; development of tolerance phenomena with regard to drugs and/or medicines, in particular with regard to opioids, gastro-oesophageal reflux syndrome, for diuresis, for antinatriuresis, for influencing the cardiovascular system, for anxiolysis, for increasing vigilance, for increasing libido, for modulating locomotor activity, and for local anaesthesia.

The pharmaceutical preparation according to the invention may assume the form of a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or be in multiparticulate form, for example in the form of pellets or granules, optionally press-moulded into tablets, packaged in capsules or suspended in a liquid and also be administered as such.

In addition to at least one salt according to the invention, optionally in the form of the pure stereoisomers thereof, in particular enantiomers or diastereomers, the racemate thereof or in the form of mixtures of the stereoisomers, in particular the enantiomers or diastereomers, in any desired mixing ratio, the pharmaceutical preparation according to the invention (the pharmaceutical composition according to the invention) conventionally contains further physiologically acceptable pharmaceutical auxiliary substances, which may preferably be selected from the group consisting of excipient materials, fillers, solvents, diluents, surface-active substances, colorants, preservatives, disintegrants, slip agents, lubricants, aromas and binders.

Selection of the physiologically acceptable auxiliary substances and the quantities thereof which are to be used depends upon whether the pharmaceutical preparation (pharmaceutical composition) is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Suitable percutaneous administration preparations also include depot preparations in dissolved form or in a dressing, optionally with the addition of agents promoting skin penetration.

Orally or percutaneously administrable formulations may release the particular salts of the invention in delayed manner.

Production of the pharmaceutical preparations according to the invention proceeds with the assistance of conventional means, devices, methods and processes well known to the person skilled in the art, such as are described for example in "Remington's Pharmaceutical Sciences", ed. A.R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the particular salts according to the invention to be administered to the patient may vary and is for example dependent on the weight or age of the patient and on the mode of administration, the indication and the severity of the complaint. Conventionally, at least one such compound is administered in a quantity of 0.005 to 5000 mg/kg, preferably of 0.05 to 500 mg/kg, of patient body weight.

EXAMPLES

Certain embodiments of the present invention may be further understood by reference to the following specific examples. These examples and the terminology used herein is for the purpose of describing particular embodiments only and is not intended to be limiting.

In all the DSC measurements (unless stated otherwise), the heating rates are to 10° C./minute; the stated temperatures are peak maxima.

A) Production of (+)-(1R,2R)-3-[2-(dimethylamino) methyl-(cyclohex-1-yl)]-phenol maleate

Example A1

Production as Crystalline form A 0.0685 g of (+)-(1R,2R)-3-[2-(dimethylamino)methyl-(cyclohex-1-yl)]-phenol are dissolved in 0.4 ml of ethyl acetate. In addition, a second solution of 0.0371 g of maleic acid in 1 ml of ethyl acetate is prepared. The two solutions are combined at room temperature and mixed with stirring, a white precipitate forming immediately. The mixture is heated with stirring to 50° C. and thereafter cooled again to room temperature. Then the precipitate is filtered out using a sintered glass filter, washed with 4 ml of ethyl acetate and the residue is dried by having air drawn through it for 5 minutes. 0.0870 mg (85% of theoretical) of (+)-(1R,2R)-3-[2-(dimethylamino)methyl-(cyclohex-1-yl)]-phenol maleate is obtained as a white, crystalline solid with a melting point of approx. 167° C. and the enthalpy of fusion is approx. 135 J/g, determined by Differential Scanning Calorimetry (DSC) at a heating rate of 10° C./minute. The crystalline solid is the polymorphic form A, whose X-ray diffraction pattern is shown in FIG. 1. The Raman spectrum is shown in FIG. 2.

If twice the quantity of (+)-(1R,2R)-3-[2-(dimethylamino) methyl-(cyclohex-1-yl)]-phenol is used, again only the 1:1 maleate is formed.

Example A2

Production as Crystalline Form A 6.22 g (53.5 mmol) of maleic acid are dissolved in a glass flask in 130 ml of ethyl acetate and then added dropwise with stirring to a solution, adjusted to a temperature of 50° C., of 12.48 g (53.5 mmol) of (+)-(1R,2R)-3-[2-(dimethylamino) methyl-(cyclohex-1-yl)]-phenol in 40 ml of ethyl acetate. After the addition of 20 to 25 ml, a white precipitate forms. After addition of the entire solution, the finely crystalline white solid is filtered out of the warm solution and washed with a little cold ethyl acetate. The residue is dried by having air drawn through it. 18.38 g (98.3% of theoretical) of (+)-(1R,2R)-3-[2-(dimethylamino)methyl-(cyclohex-1-yl)]-phenol maleate are obtained as crystalline form A (according to the X-ray diffraction pattern) with a melting point of 177-179° C. DSC analysis reveals two peaks at 165.5 and 177.2° C.

10 g of the solid are dried overnight in the drying cabinet at 40° C. and 80 to 90 mbar. The weight loss amounts to only 3.8 mg (ethyl acetate). The X-ray diffraction pattern corresponds to form A; the DSC peaks are almost unchanged 165.8 and 176.7.

Example A3

Production as Crystalline Form B

In a glass flask, 1.95 g of (+)-(1R,2R)-3-[2-(dimethylamino)methyl-(cyclohex-1-yl)]-phenol are dissolved at room temperature in 40 ml of ethyl acetate. Then a solution of 0.97 g of maleic acid in 25 ml of ethyl acetate is added dropwise at room temperature. After the addition of approx. half the solution, firstly turbidity forms and then a crystalline precipitate. The suspension is stirred at 70° C. for an hour in a rotary evaporator and then cooled to room temperature. The suspension is then cooled to 4° C. in the refrigerator and the precipitate filtered out. The solid residue is washed once with 4 ml of ethyl acetate and dried by having air drawn through it (5 minutes). 2.815 g (96.4% of theoretical) of (+)-(1R,2R)-3-[2-(dimethylamino)methyl-(cyclohex-1-yl)]-phenol maleate are obtained as crystalline form B (according to the X-ray diffraction pattern) with a melting point of 177-179° C. DSC analysis reveals a peak at 177.7° C.

Example A4

Production as Crystalline Form A 8.92 g of maleic acid are dissolved at 55° C. in a glass flask in 120 ml of ethyl acetate. In another glass flask 17.96 g of (+)-(1R,2R)-3-[2-(dimethylamino)methyl-(cyclohex-1-yl)]-phenol are likewise dissolved at 55° C. at room temperature in 108 ml of ethyl acetate and slowly added dropwise within 30 minutes to the solution of maleic acid. After the addition of approx. half, a white, voluminous, finely crystalline solid precipitates out. The suspension is stirred for a further 3 hours at 55° C. once addition is complete. It is then left to cool by itself to room temperature and stirred again overnight. The precipitate is filtered out and washed once with 20 ml of ethyl acetate and dried by having air drawn through it (5 minutes). 26.26 g (97.7% of theoretical) of (+)-(1R,2R)-3-[2-(dimethylamino)methyl-(cyclohex-1-yl)]-phenol maleate are obtained as crystalline form A (according to the X-ray diffraction pattern). DSC analysis reveals two peaks at 166.03 and 177.03° C.

Example A5

Production as Crystalline Form A 2.33 g of (+)-(1R,2R)-3-[2-(dimethylamino)methyl-(cyclohex-1-yl)]-phenol are dissolved at room temperature in 15 ml of ethyl acetate and 1.16 g of maleic acid are dissolved in 30 ml of ethyl acetate, each in a glass flask. In another glass flask, 20 ml of ethyl acetate are heated to 45° C. and then both solutions are added simultaneously dropwise with stirring. Considerable turbidity forms spontaneously. Once addition is complete, the suspension is stirred for another 3 hours at 50° C. Then it is left to cool by itself to room temperature. The precipitate is filtered out and washed once with 10 ml of ethyl acetate and dried by having air drawn through it (5 minutes). 3.41 g (97.7% of theoretical) of (+)-(1R,2R)-3-[2-(dimethylamino)methyl-(cyclohex-1-yl)]-phenol maleate are obtained as crystalline form A (according to the X-ray diffraction pattern). DSC analysis reveals two peaks at 166.03 and 177.03° C.

Example A6

Production of Crystalline (+)-(1R,2R)-3-[2-(dimethylamino)methyl-(cyclohex-1-yl)]-phenol maleate a) Production 24.64 g of (+)-(1R,2R)-3-[2-(dimethylamino)methyl-(cyclohex-1-yl)]-phenol (purity according to HPLC analysis 76.8%) are dissolved in a 1 l three-necked flask in 500 ml of ethyl acetate. The temperature is raised to 55° C. and 9.44 g of maleic acid are added all at once with stirring. Stirring is performed at this temperature for 4 hours and then for 2 hours at 20° C. Then the precipitate is filtered out, washed once with 20 ml of ethyl acetate and then dried by drawing air through it. Thermoanalysis (DSC) reveals endothermic signals at 150.4° C. and 157.7° C. Purity (relative to the phenol) amounts according to HPLC analysis to 84.4%. The yield amounts to 27.57 g (97.0% of theoretical).

b) Purification by means of stir-washing

The resultant crude product is weighed out into glass flask, combined with solvent and shaken in a Thermomixer at 50° C. for 4 hours. Then the solutions are cooled overnight to 23° and subsequently filtered. The yield and purity (HPLC) of the residue are determined. Further details may be found in Table 1 below. The following abbreviations are used: EtAc is ethyl acetate, EtOH is ethanol, PrOH is i-propanol, AcNi is acetonitrile, Tol is toluene, Hex is n-hexane, hexane, DiEt is diethyl ether, BuMe is t-butyl methyl ether, Ace is acetone, MeEt is methyl ethyl ketone, THF is tetrahydrofuran.

TABLE 1

| Maleate quantity (mg) | Solvent 1 (ml) | Solvent 2 (ml) | Yield (%) | Purity (%) |
| --- | --- | --- | --- | --- |
| 56.3 | EtAc (1.0) | — | 97.2 | 84.6 |
| 55.9 | PrOH (1.0) | — | 73.0 | 96.7 |
| 56.2 | Hex (1.0) | — | 96.3 | 84.0 |
| 55.8 | AcNi (1.0) | — | 71.5 | 93.6 |
| 56.4 | Tol (1.0) | — | 97.2 | 84.0 |
| 62.6 | DiEt (1.0) | — | 97.0 | 84.6 |
| 53.5 | BuMe (1.0) | — | 97.4 | 84.2 |
| 55.2 | Ace (1.0) | — | 58.2 | 97.9 |
| 55.1 | MeEt (1.0) | — | 75.9 | 92.1 |
| 58.8 | THF (1.0) | — | 80.1 | 89.5 |
| 55.2 | Ace (0.98) | EtOH (0.02) | 52.0 | 97.9 |
| 60.4 | Ace (0.96) | EtOH (0.04) | 50.5 | 97.0 |
| 55.5 | Ace (0.94) | EtOH (0.06) | 37.1 | 98.2 |
| 58.2 | Ace (0.92) | EtOH (0.08) | 42.4 | 98.3 |
| 57.3 | Ace (0.90) | EtOH (0.10) | 39.6 | 98.2 |
| 517.1 | PrOH (10.0) | — | 79.7 | 88.9 |
| 516.5 | PrOH (10.0) | — | 79.4 | 87.5 |
| 511.2 | PrOH (10.0) | — | 80.7 | 89.0 |
| 516.4 | Ace (10.0) | — | 62.0 | 98.1 |
| 515.2 | Ace (10.0) | — | 64.8 | 96.4 |
| 511.6 | Ace (10.0) | — | 68.7 | 94.8 |
| 506.9 | THF (10.0) | — | 82.9 | 87.9 |
| 511.2 | THF (10.0) | — | 81.9 | 87.8 |
| 507.2 | THF (10.0) | — | 83.8 | 88.5 |
| 518.3 | Ace (9.70) | EtOH (0.3) | 48.3 | 98.6 |
| 514.3 | Ace (9.70) | EtOH (0.3) | 50.9 | 97.8 |
| 509.8 | Ace (9.70) | EtOH (0.3) | 50.2 | 98.7 |

The product may be obtained in good to excellent purities by purifying the crude product by means of stir-washing.

B) Production of amorphous (+)-(1R,2R)-3-[2-(dimethylamino)methyl-(cyclohex-1-yl)]-phenol maleate Example B1

Freeze Drying 81.5 mg of the maleate produced according to Example A1 are dissolved in 3 ml of water and then quenched to −75° C. Then freeze-drying is performed at this temperature and a pressure of 0.011 mbar for 23 hours. A solid, white residue, which has a tendency to crystallise rapidly in the presence of moisture, is obtained quantitatively, substantially with formation of the crystalline form A. Differential Scanning Calorimetry (DSC, heating rate 10° C./minute) reveals a glass transition temperature of around 30° C. An exothermic peak at 85° C. is attributed to crystallisation. The crystalline material formed melts at 178° C.

If 20 mg of the amorphous form is stored at room temperature and 20% or 90% atmospheric humidity for 24 hours, there is obtained respectively a mixture of crystalline forms A and B or only crystalline form A.

C) Production of crystalline form A

The crystal shape is determined, if not stated otherwise, by comparing the Raman spectra.

Example C1

Precipitation with Non-solvent a) Precipitation with n-heptane 80 mg of the maleate produced according to Example A1 are dissolved at room temperature in 8 ml acetone. Thereafter 7.5 ml of n-heptane are added with stirring. A white precipitate is formed, which is filtered out and dried in a stream of air at room temperature. 50 mg of white powder are obtained, which corresponds to crystalline form A.

b) Precipitation with n-heptane 80 mg of the maleate produced according to Example A1 are dissolved at room temperature in 17 ml of tetrahydrofuran (THF). Thereafter 9 ml of n-heptane are added with stirring. A white precipitate is formed, which is filtered out and dried in a stream of air at room temperature. 52 mg of white powder are obtained, which corresponds to crystalline form A.

c) Precipitation with tert-butyl methyl ether (TBME)

80 mg of the maleate produced according to Example A1 are dissolved at room temperature in 21 ml of THF. Thereafter 7.5 ml of TBME are added with stirring. A white precipitate is formed, which is filtered out and dried in a stream of air at room temperature. 48 mg of white powder are obtained, which corresponds to crystalline form A.

Example C2

Phase Equilibria with Suspensions a) Suspension in acetone 0.5 ml of acetone are added to 80 mg of the maleate produced according to Example B1 and stirring is performed for 24 hours at room temperature. Filtering out is then performed, followed by drying at room temperature in a stream of air. 52 mg of crystalline form A are obtained as white powder.

b) Suspension in 1,4-dioxane 0.5 ml of 1,4-dioxane are added to 80 mg of the maleate produced according to Example B1 and stirring is performed for 24 hours at room temperature. Filtering out is then performed, followed by drying at room temperature in a stream of air. 47 mg of crystalline form A are obtained as white powder.

c) Suspension in ethyl acetate 0.5 ml of ethyl acetate are added to 80 mg of the maleate produced according to Example B1 and stirring is performed for 24 hours at room temperature. Filtering out is then performed, followed by drying at room temperature in a stream of air. 50 mg of crystalline form A are obtained as white powder.

d) Suspension in water 0.1 ml of water and then two 0.2 ml portions of water are added to 80 mg of the maleate produced according to Example B1 and stirring is performed for 24 hours at room temperature. Filtering out is then performed, followed by drying at room temperature in a stream of air. 49 mg of crystalline form A are obtained as white powder.

e) Suspension in isopropanol 0.5 ml of isopropanol are added to 80 mg of the maleate produced according to Example B1 and stirring is performed for 24 hours at room temperature. Filtering out is then performed, followed by drying at room temperature in a stream of air. 54 mg of crystalline form A are obtained as white powder.

f) Suspension in tetrahydrofuran 0.5 ml of THF are added to 80 mg of the maleate produced according to Example B1. A solid agglomerate is formed, which is comminuted with a spatula. The resultant suspension is stirred thereafter for 24 hours at room temperature. Filtering out is then performed, followed by drying at room temperature in a stream of air. 49 mg of crystalline form A are obtained as white powder.

Example C3

Crystallisation a) Crystallisation from methanol/methylene chloride 100 mg of the maleate produced according to Example A1 are dissolved in 1 ml of methanol. After the addition of 14 ml of methylene chloride, a clear solution is obtained, which is left to stand for 5 days at 5° C. Then the volume is evaporated down to a quarter and again left to stand at 5° C. for one week. Then the solvent is evaporated completely at room temperature. 98 mg of crystalline form A are obtained in the form of a white powder.

b) Crystallisation from toluene and acetone 60 mg of the maleate produced according to Example A1 are dissolved in 10 ml of toluene/acetone (1:1 vol/vol) at 60° C. and thereafter cooled to room temperature. The solution is then left to stand at 5° C. for 4 days. Thereafter, the large crystals formed are filtered out and dried. 28 mg of crystalline form A are obtained in the form of white crystals.

c) Crystallisation from ethyl acetate 51 mg of the maleate produced according to Example A1 are dissolved at 65° C. in 31 ml of ethyl acetate. The solution is then left to cool to room temperature and within 2 hours acicular crystals form. The solution is left to stand for a further 5 days at 5° C. and the crystals are filtered out and dried. 33 mg of crystalline form A are obtained in the form of white, acicular crystals.

d) Crystallisation from tetrahydrofuran 100 mg of the maleate produced according to Example A1 are dissolved at 65° C. in 7 ml of THF and thereafter cooled to room temperature. The solution is then left to stand at 5° C. for 4 days. Thereafter, the large crystals formed are filtered out and dried. 28 mg of crystalline form A are obtained in the form of large, white crystals.

e) Crystallisation from isopropanol

In a stirring flask, 2.31 g of the maleate salt produced according to Example A6a are suspended in 30 ml of isopropanol and heated within 20 minutes at a speed of rotation of the stirrer of approx. 600 rpm (revolutions per minute) to 80° C. with formation of a clear solution. The speed of rotation is increased to 800 rpm and stirring is performed at this temperature for 30 minutes, the speed of rotation being increased briefly to 1000 rpm towards the end. Then the temperature is lowered within 25 minutes to 65° C. and stirring is performed for 35 minutes at this temperature. Thereafter seeding is performed with 50 mg of crystalline form A of the maleate salt and the temperature is lowered to 10° C. with stirring within 3 hours at a rate of 0.3 K/min. The white solid is filtered out and dried in air (2.132 g, 92.3%). According to an X-ray powder diffractogram, only lines of the crystalline form A are measured. Thermoanalysis (DSC) reveals endothermic signals at 165.8° C. and 177.2° C. When thermogravimetric analysis is performed, significant weight loss is observed, such that no solvated form can be present. Purity amounts to 99.5%, determined by HPLC.

f) Crystallisation from isopropanol

In a stirring flask, 2.32 g of the maleate salt produced according to Example A6a are suspended in 30 ml of isopropanol and heated within 15 minutes at a speed of rotation of the stirrer of approx. 600 rpm (revolutions per minute) to 80° C. with formation of a clear solution. The speed of rotation is increased to 800 rpm and stirring is performed at this temperature for 20 minutes, the speed of rotation being increased briefly to 1000 rpm towards the end. Then the temperature is lowered within 10 minutes to 65° C. and stirring is performed for 10 minutes at this temperature. Thereafter seeding is performed with 50 mg of crystalline form A of the maleate salt and the temperature is lowered to 20° C. with stirring within 3 hours at a rate of 0.25 K/min. The white solid is filtered out and dried in air (2.132 g, 92.3%). According to an X-ray powder diffractogram, only lines of the crystalline form A are measured. Thermoanalysis (DSC) reveals endothermic signals at 163.4° C. and 174.4° C. When thermogravimetric analysis is performed, significant weight loss is observed, such that no solvated form can be present. Purity amounts to 99.5%, determined by HPLC.

Examlpe C4

Crystallisation by Means of Solvent Evaporation a) Solvent acetone/THF 10 mg of the maleate produced according to Example A1 are dissolved in 15 ml of acetone/THF (1:1, vol/vol) and the solvent mixture is evaporated slowly to dryness at room temperature in a stream of nitrogen. 9 mg of crystalline form A are obtained in the form of a white powder.

b) Solvent acetone/ethyl acetate 10 mg of the maleate produced according to Example A1 are dissolved in 15 ml of acetone/ethyl acetate (1:1, vol/vol) and the solvent mixture is evaporated slowly to dryness at room temperature in a stream of nitrogen. 8 mg of crystalline form A are obtained in the form of a white powder.

c) Solvent methylene chloride 10 mg of the maleate produced according to Example A1 are dissolved in 15 ml of methylene chloride (1:1, vol/vol) and the solvent mixture is evaporated slowly to dryness at room temperature under ambient conditions in an open atmosphere. 9 mg of crystalline form A are obtained in the form of a white powder.

d) Solvent THF/water 200 mg of the maleate produced according to Example A1 are dissolved in 4 ml of water/THF (1:1, vol/vol) and the solution is filtered through a 0.22 μm filter. The solution is introduced into a Petri dish and the solvent mixture is evaporated slowly to dryness at room temperature under ambient conditions in an open atmosphere. 188 mg of crystalline form A are obtained in the form of a acicular crystals.

e) Solvent THF/water 200 mg of the maleate produced according to Example A1 are dissolved in 4 ml of water/THF (1:1, vol/vol) and the solution is filtered through a 0.22 μm filter. The solution is introduced into a Petri dish and seeded with crystals of polymorph B and the solvent mixture is evaporated slowly to dryness at room temperature under ambient conditions in an open atmosphere. After one day, acicular crystals form. 160 mg of crystalline form A are obtained in the form of acicular crystals.

e) Solvent THF/water 200 mg of the maleate produced according to Example A1 are dissolved in 4 ml of water/THF (1:1, vol/vol) and the solution is filtered through a 0.22 μm filter. The solution is introduced into a Petri dish and the solvent mixture is evaporated to dryness at room temperature under a stream of nitrogen. After one day, acicular crystals form. 182 mg of crystalline form A are obtained in the form of acicular crystals.

g) Solvent 1,4-dioxane 11 mg of the maleate produced according to Example A1 are dissolved in 15 ml of 1,4-dioxane. The solution is introduced into an open vial and the solvent is evaporated to dryness under ambient conditions in an open atmosphere at room temperature within 4 days. 9 mg of crystalline form A are obtained in the form of a white powder.

h) Solvent THF 10 mg of the maleate produced according to Example A1 are dissolved in 15 ml of THF. The solution is introduced into a Petri dish and the solvent mixture is evaporated slowly to dryness at room temperature under ambient conditions in an open atmosphere within 2 days. 9 mg of crystalline form A are obtained in the form of a white powder.

i) Solvent THF/water 150 mg of the maleate produced according to Example A1 are dissolved in 3 ml of THF/water (1:1, vol/vol). Then the solvent is evaporated at 60° C. in a rotary evaporator. 135 mg of crystalline form A are obtained in the form of a white powder.

j) Solvent THF/water 150 mg of the maleate produced according to Example A1 are dissolved in 3 ml of THF/water (1:1, vol/vol). Then stirring is performed at 40° C. for 10 minutes and thereafter for 1 more minute at 60° C. Filtration is performed through a 0.22 μm filter. The solution is introduced into a Petri dish and the solvent mixture is evaporated to dryness at room temperature under a stream of nitrogen. 125 mg of crystalline form A are obtained in the form of a white powder.

k) Solvent THF 50 mg of the maleate produced according to Example A1 are dissolved at 60° C. in 40 ml of THF. Then the solution is cooled with dry ice and left to stand at −20° C., turbidity forming. After 3 days, a white precipitate has formed, which is filtered out and dried. 21 mg of crystalline form A are obtained in the form of a white powder.

Example C5

Conversion of Crystalline Form B Into Form A a) Phase equilibrium with suspension in ethyl acetate 30 mg of the crystalline form B produced according to Example D1 are suspended in 2 ml of ethyl acetate and stirred for 18 hours at 23° C. Then filtration is performed and the residue dried. 15 mg of crystalline form A are obtained in the form of a white powder.

b) Phase equilibrium with suspension in toluene 30 mg of the crystalline form B produced according to Example D1 are suspended in 2 ml of toluene and stirred for 18 hours at 23° C. Then filtration is performed and the residue dried. 22 mg of crystalline form A are obtained in the form of a white powder.

D) Production of crystalline form B

Example D1

250 mg of the maleate produced according to Example A1 are dissolved in 5 ml of THF/water (1:1, vol/vol). Then the solvent mixture is evaporated at 90° C. in a rotary evaporator. 208 mg of crystalline form B are obtained in the form of a white powder. The melting point is approx. 178° C. and the enthalpy of fusion is approx. 125 J/g, measured with DSC at a heating rate of 10° C./minute. The X-ray diffraction pattern is shown in FIG. 3 and the Raman spectrum in FIG. 4.

Example D2

The procedure is as for Example D1, except that the solvent is left to stand for 22 hours prior to evaporation. The residue is crystalline form B.

Example D3

100 mg of the maleate produced according to Example A1 are dissolved in 2 ml of THF/water (1:1, vol/vol). Then the solution is left to stand for 3.5 hours at room temperature. Thereafter the solvent mixture is evaporated at 90° C. in a rotary evaporator. 84 mg of crystalline form B are obtained in the form of a white powder.

Example D4

Two 250 mg portions of the maleate produced according to Example A1 are dissolved in each case in 5 ml of THF/water (1:1, vol/vol). One solution is filtered through a 0.22 lum filter and the second solution is filtered through a 0.45 μm filter. The solutions are each introduced into a Petri dish and the solvent mixture is evaporated slowly at room temperature under ambient conditions in an open atmosphere. After one day, spherical crystals are observed to form. After 3 days, the solvent mixture is evaporated and the residues consist of crystalline form B in the form of spherical crystals.

E) Stability investigations

Example E1

Storage of the Amorphous Form Under Elevated Atmospheric Humidity

The amorphous form according to Example B1 is stored at room temperature and 75% relative atmospheric humidity and samples are investigated after 2 days, 1, 2, 3, 4 and 8 weeks using Raman spectroscopy. After 2 days, a mixture of crystalline forms A and B is present. The same mixture is still observed after 8 weeks.

Example E2

Storage of Crystalline Form A Under Elevated Atmospheric Humidity

The maleate produced according to Example A1 is stored at room temperature and 75% relative atmospheric humidity and samples are investigated after 3 days, 1, 2, 3, 4, 8 and 10 weeks using Raman spectroscopy. The samples are virtually unchanged even after 10 weeks.

Example E3

Storage of Crystalline Form B Under Elevated Atmospheric Humidity

The crystalline form B produced according to Example D1 is stored at room temperature and 75% relative atmospheric humidity and samples are investigated after 3 days, 1, 2, 3, 4 and 8 weeks using Raman spectroscopy. The samples are virtually unchanged even after 8 weeks.

Example E4

Stability Under Grinding Conditions a) Crystalline form A on trituration

The maleate produced according to Example A1 is triturated with a pestle in a mortar for 5 minutes. Thereafter, the crystalline form A is present in unchanged form. Amorphous fractions are not observed.

b) Crystalline form B on trituration

Crystalline form B according to Example D1 is triturated with a pestle in a mortar for 5 minutes. Thereafter a mixture of crystalline forms A and B is present.

c) Crystalline form A on grinding

The maleate produced according to Example A1 is introduced into an agate ball mill (Retsch MM200 mixing mill with 5 mm agate ball) and ground at 20 Hz and room temperature for 180 minutes. Thereafter, the crystalline form A is present in unchanged form. Amorphous fractions are not observed.

d) Crystalline form B on grinding

The procedure is carried out in accordance with Example E4c) with crystalline form B according to Example D1. After 180 minutes, a mixture of crystalline forms A and B is present.

Example E5

Stability Under Pressure a) Crystalline form A on tablet pressing

The maleate produced according to Example A1 is introduced into a tablet press and pressed under a vacuum at a pressure of 100 MPa for 60 minutes to form a tablet. Thereafter, the crystalline form A is present in unchanged form.

b) Crystalline form B on tablet pressing

The procedure is carried out in accordance with Example E5a) with crystalline form B according to Example D1. After 60 minutes, a mixture of crystalline forms A and B is present.

Example E6

Water Absorption

Water absorption is determined by means of dynamic water vapour absorption (Dynamic Vapour Sorption, DVS) using apparatus DVS-1 from Surface Measurement System Ltd. The sample is placed in a platinum crucible at the tip of a microchemical balance. Then the sample is firstly equilibrated at 50% relative atmospheric humidity and then subjected to a predefined measuring program. The temperature is 25° C. The change in weight of the sample is determined.

a) Amorphous form

The amorphous form exhibits pronounced water absorption of approx. 2.2 wt. % up to approx. 33% relative atmospheric humidity. At higher atmospheric humidity, the weight drops again, which is caused by crystallisation. After the end of the test, a mixture of crystalline forms A and B is present.

b) Crystalline form A

Crystalline form A exhibits water absorption of only approx. 0.2 wt. %. At the end of the measuring cycle, the unchanged crystalline form A is substantially present.

c) Crystalline form B

Crystalline form B exhibits water absorption of only approx. 0.2 wt. %. At the end of the measuring cycle, however, a mixture of crystalline forms A and B is present.

Example E7

Stability at Elevated Temperature

The crystalline forms are stored in open and closed vessels and, after a predetermined time, possible changes are measured chromatographically (HPLC) as stability parameters. Crystalline form A proves very stable with regard to chemical stability and crystal shape. Crystalline form A proves very stable with regard to chemical stability. The results are shown in Table 2 below.

TABLE 2

| Polymorph | Conditions | Time | HPLC | FT Raman[1] |
|---|---|---|---|---|
| A | 40° C./75% R.H. | 1 week | 100.2% | A |
| A | 60° C./75% R.H. | 4 weeks | 100.3% | A |
| A | 60° C. (closed) | 1 week | 100.2% | A |
| A | 60° C. (closed) | 4 weeks | 100.5% | A |
| A | −18° C. (reference) | 4 weeks | 100% | A |
| B | 40° C./75% R.H. | 1 week | 100.3% | A and B |
| B | 60° C./75% R.H. | 4 weeks | 101.1% | A and B |
| B | 60° C. (closed) | 1 week | 100.6% | A and B |
| B | 60° C. (closed) | 4 weeks | 100.9% | A and B |
| B | −18° C. (reference) | 4 weeks | 100% | A and B |

[1]Determination of crystalline form

Example E8

Water Absorption of Maleate and Hydrochloride (Comparison)

Water absorption is determined by means of dynamic water vapour absorption (Dynamic Vapour Sorption, DVS) using apparatus DVS-1 from Surface Measurement System Ltd. The sample is placed in a platinum crucible at the tip of a microchemical balance. Then the sample is firstly equilibrated at 50% relative atmospheric humidity and then subjected to a predefined measuring program. The temperature is 25° C. The change in weight of the sample is determined after a stepwise increase in relative atmospheric humidity by 10% steps up to 90%.

a) (+)-(1R,2R)-3-[2-(dimethylamino)methyl-(cyclohex-1-yl)]-phenol maleate (form A)

Decidedly low water absorption of 0.06% is revealed. The absorbed moisture is released again completely at approx. 10% relative atmospheric humidity.

b) (+)-(1R,2R)-3-[2-(dimethylamino)methyl-(cyclohex-1-yl)]-phenol hydrochloride (form D)

When the relative atmospheric humidity is increased to approx. 75%, water absorption of approx. 2 wt. % is observed. A further increase to 90% relative atmospheric humidity results in water absorption of altogether approx. 5 wt. %. In the case of desorption by lowering the relative atmospheric humidity in 10% steps, more water is released than was previously absorbed, namely 8.5% altogether. It is suspected that a variable hydrate is present.

Example E9

Damp Storage and Drying of Maleate and Hydrochloride (Comparison)

Maleate and hydrochloride according to Example E8 are stored firstly at 25° C. and 75% and 95% relative atmospheric humidity for 7 days and thereafter are dried for 7 days in the drying cabinet at 50° C. under a vacuum. Before storage begins, X-ray diffraction patterns (XRD) are recorded, DSC performed to determine transition points (Tp), dry weight (DW) and the Karl-Fischer water content (WC) are determined and the same values again after damp storage and drying. The X-ray diffraction patterns show no change in crystalline forms A and D after damp storage and drying. The initial vales for the hydrochloride are Tp=116.27° C., DW=6.35% and WC 8.00%. The initial values for the maleate are Tp=170.4° C. and 179.85° C., DW=0 and WC=0.2%. The results are given in Tables 3 (75% relative atmospheric humidity) and 4 (95% relative atmospheric humidity).

TABLE 3

(75%):

| Salt | Tp (° C.) | DW (%) | WC (%) | Tp (° C.) | DW (%) | WC (%) |
|---|---|---|---|---|---|---|
| Maleate | 165.41 | — | 0.20 | 165.33 | — | 0.20 |
| Hydrochloride | 116.22 | 5.92 | 8.50 | 113.83 | 6.12 | 6.00 |

TABLE 4

(95%):

| Salt | Tp (° C.) | DW (%) | WC (%) | Tp (° C.) | DW | WC (%) |
|---|---|---|---|---|---|---|
| Maleate | 165.92 | — | 0.20 | 165.47 | — | 0.50 |
|  | 177.82 |  |  | 177.55 |  |  |
| Hydrochloride | 116.52 | 7.84 | 8.50 | 114.47 | 6.74 | 6.60 |

Equipment, Methods:

Differential Scanning Calorimetry (DSC): model Perkin Elmer DSC 7 or Perkin Elmer Pyris 1. Variable measurements (heating rate) in gold or aluminium crucibles.

Powder X-Ray Diffraction Patterns (PXRD):

PXRD is performed using a Philips 1710 Powder X-ray diffractometer, CuK$_\alpha$ radiation being used. D spacing is calculated from the 2theta values, the wavelength of 1.54060 Å being taken as basis. It is the case in general that the 2theta values have an error rate of ±0.1-0.2°. In the case of the d spacing values, therefore, the experimental error depends on the location of the line (of the peak).

Raman Spectroscopy:

FT Raman spectra are recorded using a Bruker RFS 100 FT-Raman system, which is operated with an Nd:YAG laser (wavelength 1064 nm) and a germanium detector cooled with liquid nitrogen. For each sample, 64 scans are accumulated with a resolution of 2 cm$^{-1}$. In general, a laser power of 100 mW is used.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereto.

What is claimed is:

1. A crystalline form of a 3-[2-(dimethylamino)methyl-(cyclohex-1-yl)]-phenol maleate compound corresponding to formula I and having a powder diffractogram comprising one or more of the following reflections: 9.38, 9.94 and 10.35, and a Raman spectrum comprising the following bands, in each case expressed in wavenumbers (cm-1): 118 (vs), 188 (w), 400 (w), 676 (vw), 2812 (w), 2879 (m).

2. The compound of claim 1, wherein the compound has the 1R, 2R configuration.

3. The crystalline form of a 3-[2-(dimethylamino)-methyl-(cyclohex-1-yl)]-phenol maleate compound according to claim 1, having a powder diffractogram additionally comprising the following reflections: 12.76, 15.94, 17.54, 19.28, 28.68 and 31.99 (in each case ±0.2 in 2 θ).

4. The crystalline form of a 3-[2-(dimethylamino)-methyl-(cyclohex-1-yl)]-phenol maleate compound according to claim 1, having a Raman spectrum comprising the following bands, in each case expressed in wavenumbers (cm-1):

118 (vs), 188 (w), 292 (m), 328 (m), 359 (w), 400 (w), 486 (vw), 676 (vw), 901 (w), 1025 (w), 1273 (m), 1351 (m), 1412 (w), 1569 (vw), 1601 (m), 1690 (m), 2812 (w), 2879 (m), 2986 (m), 3060 (m).

5. The compound of claim 4, wherein the compound has the 1R, 2R configuration.

6. A crystalline form of a 3-[2-(dimethylamino)methyl-(cyclohex-1-yl)]-phenol maleate compound corresponding to formula I (I)

and which exhibits an X-ray diffraction pattern as shown in FIG. 1 and a Raman spectrum as shown in FIG. 2.

7. The compound of claim 6, wherein the compound has the 1R, 2R configuration.

8. A crystalline form of a 3-[2-(dimethylamino)methyl-(cyclohex-1-yl)]-phenol maleate compound corresponding to formula I (I)

and having:
  a powder diffractogram comprising one or more of the following reflections: 8.36, 14.5 and 14.83, and
  a Raman spectrum comprising the following bands, in each case expressed in wavenumbers (cm-1): 229 (m), 875 (m) and 2829 (m).

9. The compound of claim 8, wherein the compound has the 1R, 2R configuration.

10. A crystalline form of a 3-[2-(dimethylamino)methyl-(cyclohex-1-yl)]-phenol maleate compound according to claim 8, wherein the powder diffractogram additionally comprises the following reflections:
  11.85, 12.19, 18.16, 22.85, 29.1 and 29.41 (in each case ±0.2 in 2θ).

11. A crystalline form of a 3-[2-(dimethylamino)methyl-(cyclohex-1-yl)]-phenol maleate compound according to claim 8, having a Raman spectrum comprising the following bands:
  229 (m), 307 (w), 372 (w), 605 (vw), 875 (m), 890 (w), 1010 (w), 1197 (m), 1401 (vw), 1480 (vw), 1583 (m), 1703 (s), 2829 (m), 2953 (s).

12. A crystalline form of a 3-[2-(dimethylamino)methyl-(cyclohex-1-yl)]-phenol maleate compound according to claim 8, which exhibits an X-ray diffraction pattern shown in FIG. 3 and a Raman spectrum as shown in FIG. 4.

13. The compound of claim 12, wherein the compound has the 1R, 2R configuration.

14. A method for treating or alleviating pain, said method comprising administering to a patient suffering from pain an effective amount of a 3-[2-(dimethylamino)methyl-(cyclohex-1-yl)]-phenol maleate compound according to claim 8.

15. A crystalline form A of a 3-[2-(dimethylamino)methyl-(cyclohex-1-yl)]-phenol maleate compound according to claim 1, having a characteristic X-ray diffraction pattern in the range from 2° to 35° 2θ with pronounced characteristic lines, expressed in d values (Å): 9.4, 6.8, 5.56, 5.30, 5.22, 4.71, 4.66, 4.24, 4.12, 4.03, 3.98, 3.76, 3.27.

16. The compound of claim 15, wherein the compound has the 1R, 2R configuration.

17. A crystalline form of a 3-[2-(dimethylamino)methyl-(cyclohex-1-yl)]-phenol maleate compound according to claim 8, having a characteristic X-ray diffraction pattern in the range from 2° to 35 ° 2θ with pronounced characteristic lines, expressed in d values (Å): 10.6, 7.5, 7.3, 6.1, 5.29, 4.88, 4.72, 4.47, 4.43, 4.26, 4.24, 3.99, 3.71, 3.52, 3.30.

18. The compound of claim 17, wherein the compound has the 1R, 2Rconfiguration.

* * * * *